United States Patent
Loerz et al.

(10) Patent No.: US 6,890,732 B1
(45) Date of Patent: May 10, 2005

(54) NUCLEIC ACID MOLECULES WHICH CODE FOR ENZYMES DERIVED FROM WHEAT AND WHICH ARE INVOLVED IN THE SYNTHESIS OF STARCH

(75) Inventors: Horst Loerz, Hamburg (DE); Stephanie Luetticke, Hamburg (DE); Martina Block, Bonn (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 09/674,824
(22) PCT Filed: May 7, 1999
(86) PCT No.: PCT/EP99/03156
§ 371 (c)(1),
(2), (4) Date: Nov. 6, 2000
(87) PCT Pub. No.: WO99/58688
PCT Pub. Date: Nov. 18, 1999

(30) Foreign Application Priority Data

May 8, 1998 (DE) .......................... 198 20 607

(51) Int. Cl.[7] .................. C12P 21/06; C12N 15/00; C12N 15/63; A01N 63/00; C07H 21/04
(52) U.S. Cl. .................. 435/69.1; 435/320.1; 435/455; 424/93.2; 424/93.21; 536/23.2; 536/23.6
(58) Field of Search .................. 435/69.1, 320.1, 435/455, 325, 410, 419; 424/93.2, 93.21; 536/23.2, 23.6

(56) References Cited

FOREIGN PATENT DOCUMENTS

| CA | 2255538 | 11/1997 |
|---|---|---|
| WO | WO 97/44472 | 11/1997 |
| WO | WO 97/45545 | 12/1997 |
| WO | WO 99/14314 | 3/1999 |

OTHER PUBLICATIONS

Rudinger, J., 1976, "Peptide Hormones", edited by Parsons, J. A., University Park Press, Baltimore, p. 1–7.*

Kaye et al., 1990, Proc. Natl. Acad. Sci. USA, vol. 87, pp. 6922–6926.*

Skolnick et al., 2000, TIBTECH, vol. 18, p. 34–39.*

Block et al., 1996, GenEmbl Accession No. U48227, p. 11, 12.*

Block et al., 1997, Geneseq Accession No. AAV01527, p. 5, 6.*

Baba et al., "Identification, cDNA Cloning, and Gene Expression of Soluble Starch Synthase in Rice (*Oryza sativa* L.) Immature Seeds", Plant Physiol., vol. 103, pp. 565–573, 1993.

* cited by examiner

*Primary Examiner*—Shin-Lin Chen
(74) *Attorney, Agent, or Firm*—Frommer Lawrence & Haug LLP

(57) ABSTRACT

Nucleic acid molecules are described which encode wheat enzymes involved in starch synthesis in plants. These enzymes are soluble wheat starch synthases. The invention furthermore relates to vectors and host cells which contain the above-described nucleic acid molecules. In particular to transformed plant cells and plants which can be regenerated from these and which have an increased or reduced activity of the soluble starch synthases according to the invention.

13 Claims, No Drawings

NUCLEIC ACID MOLECULES WHICH CODE FOR ENZYMES DERIVED FROM WHEAT AND WHICH ARE INVOLVED IN THE SYNTHESIS OF STARCH

CROSS-REFERENCE TO RELATED APPLICATIONS

This application claims the benefit of and priority to PCT Applications PCT/EP99/03156 filed May 7, 1999 and DE 198 20607.0 filed May 8, 1998.

STATEMENT REGARDING FEDERALLY SPONSORED RESEARCH AND DEVELOPMENT

Not applicable.

BACKGROUND OF THE INVENTION

The present invention relates to nucleic acid molecules which encode a wheat enzyme involved in starch synthesis in plants. This enzyme is a soluble type-1 starch synthase.

The invention furthermore relates to vectors, host cells, plant cells and plants comprising the nucleic acid molecules according to the invention.

Furthermore, there are described methods for the generation of transgenic plants which, owing to the introduction of nucleic acid molecules according to the invention, synthesize starch with altered characteristics.

In view of the increasing importance attributed lately to plant constituents as renewable raw materials, one of the objects of biotechnology research addresses the adaptation of these plant raw materials to the needs of the processing industry. Moreover, to allow renewable raw materials to be used in as many fields as possible, a wide diversity of materials must be generated.

Apart from oils, fats and proteins, polysaccharides constitute the important renewable raw materials from plants. Apart from cellulose, starch—which is one of the most important storage substances in higher plants—takes a central position amongst the polysaccharides. In this context, wheat is one of the most important crop plants since it provides approximately 20% of the total starch production in the European Community.

The polysaccharide starch is a polymer of chemically uniform units, the glucose molecules. However, it is a highly complex mixture of different molecule types which differ with regard to their degree of polymerization, the occurrence of branching of the glucose chains and their chain lengths, which, in addition, may be derivatized, for example phosphorylated. Starch therefore does not constitute a uniform raw material. In particular, amylose starch, an essentially unbranched polymer of -1,4-glycosidically linked glucose molecules, differs from amylopectin starch which, in turn, constitutes a complex mixture of glucose chains with various branchings.

The branchings occur by the occurrence of additional -1,6-glycosidic linkages. In wheat, amylose starch makes up approximately 11 to 37% of the starch synthesized.

To allow suitable starches to be used in the widest possible manner for the widest possible range of industrial needs, it is desirable to provide plants which are capable of synthesizing modified starches which are particularly well suited to various purposes. One possibility of providing such plants is to apply plant breeding measures. However, since wheat is polyploid in character (tetra- and hexaploid), the exertion of influence by plant breeding proves to be very difficult. A "waxy" (amylose-free) wheat was generated only recently by crossing naturally occurring mutants (Nakamura et al., Mol. Gen. Genet. 248 (1995), 253–259).

An alternative to plant breeding methods is the specific modification of starch-producing plants by recombinant methods. However, a prerequisite here is the identification and characterization of the enzymes which are involved in starch synthesis and/or starch modification and of the isolation of the nucleic acid molecules encoding these enzymes.

The biochemical pathways which lead to the synthesis of starch are essentially known. Starch synthesis in plant cells takes place in the plastids. In photosynthetically active tissue, these plastids are the chloroplasts, and in photosynthetically inactive, starch-storing tissue they are amyloplasts.

Important enzymes which are involved in starch synthesis are the starch synthases and the branching enzymes. Amongst the starch synthase, various isoforms have been described, all of which catalyze a polymerization reaction by transferring a glucosyl residue from ADP-glucose to $\alpha$-1,4-glucans. Branching enzymes catalyze the introduction of $\alpha$-2,6-branchings into linear $\alpha$-1,4-glucans.

Starch synthases can be divided into two classes: the starch-granule-bound starch synthases ("granule-bound starch synthases"; GBSS) and the soluble starch synthases ("soluble starch synthases"; SSS). This distinction is not unambiguous in each case since some of the starch synthases exist both in starch-granule-bound form and in solid form (Denyer et al., Plant J. 4 (1993), 191–198; Mu et al., Plant J. 6 (1994), 151–159). Various isoforms have been described, in turn, within these classes for various plant species, and these isoforms differ from each other in terms of their dependency on starter molecules (so-called primer dependent (type II) and primer-independent (type I) starch synthases).

The exact function during starch synthesis has been determined as yet only for the isoform GBSS I, [lacuna] in which this enzyme activity is greatly or fully reduced synthesize an amylose-free (so-called waxy) starch (Shure et al., Cell 35 (1983), 225–233; Visser et al., Mol. Gen-Genet. 225 (1991), 289–296; WO 92/11376), so that a decisive role in the synthesis of amylose starch is assumed to be played by this enzyme. This phenomenon is also observed in the cells of the green alga *Chlamydomonas* reinhardtii (Delrue et al., J. Bacteriol. 174 (1992), 3612–3620). Moreover, it was possible to demonstrate, in. *Chlamydomonas*, that GBSS I is not only involved in amylose synthesis, but also plays a role in amylopectin synthesis. Mutants which have no GBSS I activity lack a particular fraction of the normally synthesized amylopectin which contains longer-chain glucans.

The functions of the other isoforms of the starch-granule-bound starch m synthases, in particular of GBSS II, and of the soluble starch synthases are unclear as yet. It is assumed that the soluble starch synthases, together with branching enzymes, participate in amylopectin synthesis (see, for example, Ponstein et al., Plant Physiol. 29 (1990), 234–241) and that they play an important function in regulating the starch synthesis rate.

In wheat, at least two isoforms of the starch-granule-bound starch synthase (60 kDA and 100–105 kDA) and a further isoform which possibly represents a soluble starch synthase (Denyer et al., Planta 196 (1995), 256–265; Rahman et al., Aust. J. Plant Physiol. 22 (1995), 793–803) have been identified at protein level. The presence of several SSS isoforms has already been detected earlier with the aid of chromatographic methods (Rijven, Plant Physiol. 81 (1986), 448–453). A cDNA which encodes wheat GBSS I has already been described (Ainsworth et al., Plant Mol. Biol. 22 (1993), 67 to 82).

Nucleic acid sequences which encode wheat starch synthase isoforms or subsequences of such nucleic acids are known to date from WO 97/45545. cDNA sequences which encode starch synthases other than GBSS I have only been described for peas (Dry et al., Plant J 2 (1992), 193–202), rice (Baba et al., Plant Physiol. 103 (1993), 565 to 573) and potatoes (Edwards et al., Plant J. 8 (1995), 283 to 294) as yet. Soluble starch synthases were identified not only in wheat, but also in a series of other plant species. For example, soluble starch synthases have been isolated to homogeneity from peas (Denyer and Smith, Planta 186 (1992), 609 to 617) and potatoes (Edwards et al., Plant J 8 (1995), 283 to 294).

In these cases, it emerged that the isoform of the soluble starch synthase, which has been identified as SSS III, is identical to the starch-granule-bound starch synthase GBSS II (Denyer et al., Plant J. 4 (1993), 191 to 198; Edwards et al., Plant J. 8 (1995), 283 to 294). The presence of a plurality of SSS isoforms has been described for some other plant species with the aid of chromatographic methods, for example in the case of barley (Tyynelä and Schulman, Physiologica Plantarum 89 (1993) 835–841; Kreis, Planta 148 (1980), 412 to 416). However, DNA sequences which encode these proteins have not been described as yet.

To provide further possibilities of altering any starch-storing plants, preferably cereals, in particular wheat, so that they synthesize a modified starch, it is necessary to identify in each case DNA sequences which encode further isoforms of the starch synthases.

BRIEF SUMMARY OF THE INVENTION

The object of the present invention is therefore to provide nucleic acid molecules, in particular from wheat, encoding enzymes which are involved in starch biosynthesis, which allow genetically modified plants to be generated which make possible the production of plant starches whose chemical and/or physical characteristics are altered.

This object is achieved by providing the use forms designated in the patent claims.

DETAILED DESCRIPTION OF THE INVENTION

The present invention therefore relates to nucleic acid molecules which [lacuna] proteins with the activity of a soluble wheat starch synthase, such molecules preferably encoding proteins which essentially comprise the amino acid sequence indicated under Seq ID NO. 2. In particular, the invention relates to nucleic acid molecules which contain the nucleotide sequence stated under Seq ID No. 1 or part thereof, preferably molecules which encompass the coding region stated in Seq ID No. 1, especially preferably nucleotide No. 9 to 570 of Seq ID No. 1 and corresponding ribonucleotide sequences.

The present invention furthermore relates to nucleic acid molecules which hybridized with one of the nucleic acid molecules according to the invention.

The invention also relates to nucleic acid molecules encoding a soluble wheat starch synthase whose sequence deviates from the nucleotide sequences of the above-described molecules owing to the degeneracy of the genetic code.

The invention also relates to nucleic acid molecules with a sequence which is complementary to all or part of one of the abovementioned sequences.

The term "hybridization" as used in the context of the present invention denotes hybridization under conventional hybridization conditions, preferably under stringent conditions, as they are described, for example, by Sambrook et al., Molecular Cloning, A Laboratory Manual, 2nd Ed. (198.9) Cold Spring Harbor Laboratory Press, Cold Spring Harbor, N.Y.).

"Hybridization" especially preferably takes place under the following conditions:

| | |
|---|---|
| Hybridization buffer: | 2 × SSC; 10 × Denhardt solution (Ficoll 400 + PEG + BSA; ratio 1:1:1); 0.1% SDS; 5 mM EDTA; 50 mM Na$_2$HPO$_4$; 250 µg/ml herring sperm DNA; 50 µg/ml tRNA; or 0.25 M sodium phosphate buffer pH 7.2; 1 mM EDTA; 7% SDS |
| Hybridization temperature | T = 65 to 70° C. |
| Wash buffer: | 0.2 × SSC; 0.1% SDS |
| Wash temperature | T = 40 to 75° C. |

Nucleic acid molecules which hybridize with the nucleic acid molecules according to the invention are capable, in principle, of encoding starch synthases from any wheat plant which expresses such proteins.

Nucleic acid molecules which hybridize with the molecules according to the invention can be isolated for example from genomic libraries or cDNA libraries of wheat or wheat plant tissue. Alternatively, they can be generated by recombinant methods or synthesized chemically.

Identification and isolation of such nucleic acid molecules can be effected using the molecules according to the invention or parts of these molecules or the reverse complements of these molecules, for example by means of hybridization by standard methods (see, for example, Sambrook et al., 1989, Molecular Cloning, A Laboratory Manual, 2nd Ed. Cold Spring Harbor Laboratory Press, Cold Spring Harbor, N.Y.).

Hybridization probes which can be used are, for example, nucleic acid molecules which have exactly or essentially the nucleotide sequence stated under Seq ID No. 1, or parts of this sequence. The fragments used as hybridization probe may also be synthetic fragments which have been prepared with the aid of the customary synthetic techniques and whose sequence essentially agrees with that of a nucleic acid molecule according to the invention.

The molecules hybridizing with the nucleic acid molecules according to the invention also encompass fragments, derivatives and allelic variants of the above-described nucleic acid molecules which encode a wheat starch synthase according to the invention. Fragments are to be understood as meaning parts of the nucleic acid molecules of sufficient length so as to encode one of the proteins described. The term derivative means in this context that the sequences of these molecules differ from the sequences of the above-described nucleic acid molecules at one or more positions and have a high degree of homology with these sequences. Homology means a sequence identity of at least 40%, in particular an identity of at least 60%, preferably over 80%, especially preferably over 90%. The deviations relative to the above-described nucleic acid molecules may have been generated by deletion, substitution, insertion or recombination.

Homology furthermore means that functional and/or structural equivalence exists between the nucleic acid molecules in question or the proteins encoded by them. The nucleic acid molecules which are homologous to the above-described molecules and constitute derivatives of these molecules are, as a rule, variations of these molecules which constitute modifications exerting the same biological function. They may be naturally occurring variations, for example, sequences from other organisms, or mutations, where these mutations may have occurred naturally or were introduced by directed mutagenesis. Furthermore, the variations may be synthetically generated sequences. The allelic variants may be both naturally occurring variants and synthetically generated variants or variants produced by recombinant DNA techniques.

The proteins encoded by the various variants of the nucleic acid molecules according to the invention share certain characteristics. These may include, for example, enzyme activity, molecular weight, immunological reactivity, conformation and the like, or else physical properties such as, for example, the migration behavior in gel electrophoresis, chromatographic behavior, sedimentation coefficients, solubility, spectroscopic characteristics, charge characteristics, stability; pH optimum, temperature optimum and the like.

Important characteristics of a starch synthase are: i) their localization in the stroma of the plastids of plant cells; ii) their ability to synthesize linear α-1,4-linked polyglucans. This activity can be determined as described by Denyer and Smith (Plante 186 (1992), 606 to 617). The protein encoded by the nucleic acid molecules according to the invention is a soluble wheat type I starch synthase. These proteins have certain regions which are homologous with previously known soluble starch synthases from other plant species.

The nucleic acid molecules according to the invention may be DNA molecules, in particular cDNA or genomic molecules. Furthermore, the nucleic acid molecules according to the invention may be RNA molecules which may result, for example, from the transcription of a nucleic acid molecule according to the invention. The nucleic acid molecules according to the invention may have been obtained for example from natural sources or they may have been generated by recombinant techniques or synthesized.

The invention also relates to oligonucleotides which hybridize specifically with a nucleic acid molecule according to the invention. Such oligonucleotides preferably have a length of at least 10, in particular of at least 15 and especially preferably of at least 50 nucleotides. The oligonucleotides according to the invention are ones which hybridize specifically with nucleic acid molecules according to the invention, i.e. not or only to a very low degree with nucleic acid sequences which encode other proteins, in particular other starch synthases. The oligonucleotides according to the invention can be used, for example, as primers for a PCR reaction or as hybridization probe for the isolation of related genes. Equally, they may be constituents of antisense constructs or of DNA molecules encoding suitable ribozymes.

The invention furthermore relates to vectors, in particular plasmids, cosmids, phagemids, viruses, bacteriophages and other vectors conventionally used in genetic engineering, comprising the above-described nucleic acid molecules according to the invention. Such vectors are suitable for the transformation of pro- or eukaryotic cells, preferably of plant cells.

The vectors particularly especially permit integration of the nucleic acid molecules according to the invention, if appropriate together with flanking regulatory regions, into the genome of the plant cell. Examples are binary vectors which can be employed in agrobacterial-mediated gene transfer. Preferably, integration of a nucleic acid molecule according to the invention in sense or antisense orientation ensures that a translatable or, if appropriate, nontranslatable RNA is synthesized in the transformed pro- or eukaryotic cells.

The term "vector" generally denotes a suitable auxiliary known to the skilled worker which allows the directed transfer of a single- or double-stranded nucleic acid molecule into a host cell, for example a DNA or RNA virus, a virus fragment, a plasmid construct which, in the absence or presence of regulatory elements, may be suitable for transferring nucleic acid into cells, or support materials such as glass fiber or else metal particles as can be employed in the particle gun method, but it may also encompass a nucleic acid molecule which can be introduced directly into a cell by means of chemical or physical methods.

In a preferred embodiment, the nucleic acid molecules within the vectors are linked to regulatory elements which ensure transcription and synthesis of a translatable RNA in pro- or eukaryotic cells or which—if desired—ensure synthesis of a nontranslatable RNA.

Expression of the nucleic acid molecules according to the invention in prokaryotic cells, for example, in *Escherichia coli*, is of importance for a more detailed characterization of the enzymatic activities of the enzymes encoded by these molecules. In particular, it is possible to characterize the product synthesized by the enzymes in question in the absence of other enzymes involved in starch synthesis in the plant cell. This permits conclusions regarding the function which the protein in question exerts during starch synthesis in the plant cell.

In addition, various types of mutations can be introduced into the nucleic acid molecules according to the invention by means of customary techniques of molecular biology (see, for example, Sambrook et al., 1989, Molecular Cloning, A Laboratory Manual, 2nd Ed. Cold Spring Harbor Laboratory Press, Cold Spring Harbor, N.Y.), resulting in the synthesis of proteins whose biological properties may be altered. Possible here is, on the one hand, the generation of deletion mutants in which nucleic acid molecules are generated by successive deletions from the 5'- or the 3'-end of the coding DNA sequence which lead to the synthesis of correspondingly truncated proteins. Such deletions at the 5'-end of the nucleotide sequence allow, for example, amino acid sequences to be identified which are responsible for translocation of the enzyme into the plastids (transit peptides). This allows the directed generation of enzymes which, owing to the removal of the sequences in question, are no longer localized in the plastids, but in the cytosol, or which, owing to the addition of other signal sequences, are localized in other compartments.

On the other hand, it is also conceivable to introduce point mutations at positions where altering the amino acid sequence affects, for example, enzyme activity or enzyme regulation. In this manner, it is possible to generate, for example, mutants which have an altered $K_m$ value or which are no longer subject to the regulatory mechanisms via allosteric regulation or covalent modification which are normally present in the cell.

Furthermore, it is possible to generate mutants which have an altered substrate or product specificity of the protein according to the invention, for example by utilizing ADP-glucose-6-phosphate instead of ADP-glucose. Furthermore, it is possible to generate mutants which have an altered activity—temperature profile of the protein according to the invention.

To carry out the recombinant modification of prokaryotic cells, the nucleic acid molecules according to the invention or parts of these molecules can be introduced into plasmids which allow mutagenesis to take place or a sequence to be altered by recombining DNA sequences. Base exchanges can be carried out or natural or synthetic sequences added with the aid of standard methods (cf. Sambrook et al., 1989, Molecular Cloning: A laboratory manual, 2nd Ed., Cold Spring Harbor Laboratory Press, NY, USA). To link the DNA fragments to each other, adapters or linkers may be added to the fragments. Furthermore, manipulations may be employed which provide suitable restriction cleavage sites or which eliminate superfluous DNA or restriction cleavage sites. Where insertions, deletions or substitutions are suitable, in-vitro mutagenesis, primer repair, restriction or ligation may be employed. Analytical methods which are generally employed are sequence analysis, restriction analysis or further methods of biochemistry and molecular biology.

In a further embodiment, the invention relates to host cells, in particular pro- or eukaryotic cells, which have been transformed with an above-described nucleic acid molecule according to the invention or a vector according to the invention, and to cells which are derived from cells transformed thus and comprise a nucleic acid molecule according to the invention or a vector. They are preferably pro- or eukaryotic cells, in particular plant cells.

The invention furthermore relates to proteins with a starch synthase activity, which are encoded by the nucleic acid molecules according to the invention and which can be prepared by recombinant technology, and to processes for their preparation, where a host cell according to the invention is cultured under suitable conditions which are known to the skilled worker and which permit synthesis of the protein according to the invention, and it is subsequently isolated from the host cells and/or the culture medium.

Providing the nucleic acid molecules according to the invention now makes it possible to intervene, with the aid of recombinant methods, in a directed fashion in the starch metabolism of plants and to alter it to result in synthesis of a modified starch whose physicochemical properties, for example the amylose/amylopectin ratio, the degree of branching, the average chain length, the phosphate content, the gelatinization behavior, the gel- or film-forming properties, the starch granule size and/or the starch granule shape is altered in comparison to known starch.

Thus, it is possible to express the nucleic acid molecules according to the invention in plant cells in order to increase the activity of the starch synthase in question, or the introduction into cells which do not naturally express this enzyme. Furthermore, it is possible to modify the nucleic acid molecules according to the invention by methods known to the skilled worker in order to obtain starch synthases according to the invention which are no longer subject to the cell's intrinsic regulatory mechanisms or which have altered temperature-activity profiles or substrate or product specificities.

When expressing the nucleic acid molecules according to the invention in plants, it is possible, in principle, for the protein synthesized to be localized in any desired compartment of the plant cell. To achieve localization in a particular compartment, the sequence ensuring the localization in plastids must be deleted and the remaining coding region must, if necessary, be linked to DNA sequences which ensure the localization in the compartment in question. Such sequences are known (see, for example, Braun et al., EMBO J. 11 (1992), 3219–3227; Wolter et al., Proc. Natl., Acad. Sci. USA 85 (1988), 846–850; Sonnewald et al., Plant J. 1 (1991), 95–106).

The present invention thus also relates to a method for generating transgenic plant cells which have been transformed with a nucleic acid molecule or vector according to the invention, where a nucleic acid molecule according to the invention or a vector according to the invention is integrated into the genome of a plant cell, the transgenic plant cells which have been transformed by means of a vector or nucleic acid molecule according to the invention, and transgenic plant cells derived from cells transformed thus. The cells according to the invention comprise one or more nucleic acid molecules or vectors according to the invention, these preferably being linked 10 regulatory DNA elements which ensure transcription in plant cells, in particular to a suitable promoter. Such cells can be distinguished from naturally occurring plant cells inter alia by the fact that they comprise a nucleic acid molecule according to the invention which does not occur naturally in these cells, or by the fact that such a molecule exists integrated at a location in the cell's genome where it does not occur otherwise, i.e. in a different genomic environment. Furthermore, such transgenic plant cells according to the invention can be distinguished from naturally occurring plant cells by the fact that they comprise at least one copy of a nucleic acid molecule according to the invention stably integrated into their genome, if appropriate in addition to copies of such a molecule which occur naturally in the cells. If the nucleic acid molecule(s) introduce into the cells is (are) additional copies to molecules which already occur naturally in the cells, then the plant cells according to the invention can be distinguished from naturally occurring plant cells in particular by the fact that this additional copy, or these additional copies, is, or are, localized at locations in the genome where it does not occur naturally, or they do not occur naturally. This can be checked in a simple manner, for example, with the aid of a Southern blot analysis by methods known to the skilled worker.

If the nucleic acid molecule which has been introduced into the plant genome is heterologous to the plant cell, the transgenic plant cells exhibit transcripts of the nucleic acid molecules according to the invention which can be detected in a simple manner by methods known to the skilled worker, for example by Northern blot analysis.

If the nucleic acid molecule according to the invention which has been introduced is homologous to the plant cell, the cells according to the invention can be distinguished from naturally occurring cells, for example, on the basis of the additional expression of nucleic acid molecules according to the invention. The transgenic plant cells preferably comprise more transcripts of the nucleic acid molecules according to the invention. This can be detected, for example, by Northern blot analysis. "More" in this context means preferably at least 10% more, preferably at least 20% more, especially preferably at least 50% more transcripts than corresponding untransformed cells. The cells furthermore preferably exhibit a corresponding increase or decrease in the activity of the protein according to the invention (at least 10%, 20% or 50%). The transgenic plant cells can be regenerated into intact plants by techniques known to the skilled worker.

Another subject matter of the present invention is a method for the generation of transgenic plants, where one or more nucleic acid molecules or vectors according to the invention are integrated into the genome of a plant cell and a complete plant is regenerated from said plant cell. The plants which can be obtained by regenerating the transgenic plant cells according to the invention are also a subject matter of the present invention. The invention furthermore relates to plants which comprise the above-described transgenic plant cells. In principle, the transgenic plants can be plants of any species, i.e. not only monocotyledonous, but also dicotyledonous plants. They are preferably useful plants, by preference starch-synthesizing or starch-storing plants, especially preferably rye, barley oats, wheat, sorghum and millet, sago, maize, rice, peas, marrowfat peas, cassava, potatoes, tomatoes, oilseed rape, soy beans, hemp, flax, sunflowers, cowpeas or arrowroot, in particular wheat, maize, rice and potatoes.

The invention also relates to propagation material of the plants according to the invention, for example fruits, seeds, tubers, rootstocks, seedlings, cuttings, calli, protoplasts, cell cultures and the like.

The present invention furthermore relates to a process for the preparation of a modified starch comprising the step of extracting the starch from an above-described plant according to the invention and/or starch-storing parts of such a plant.

Processes for extracting the starch from plants or starch-storing parts of plants, in particular from wheat, are known to the skilled worker, cf., for example, Eckhoff et al. (Cereal Chem. 73 (1996) 54–57) "Starch: Chemistry and Technology (Eds.: Whistler, BeMiller and Paschall (1994), 2nd edition, Academic Press Inc. London Ltd; ISBN 0-12-746270-8; see, for example, Chapter XII, pages 412–468: Corn and sorghum starches: production; by Watson; Chapter XIII, pages 469–479; Tapioca, arrowroot and sago starches: production; by Corbishley and Miller; Chapter XIV, pages 479–490: Potato starch: production and uses; by Mitch; Chapter XV, pages 491 to 506: Wheat starch: production, modification and uses; by Knight and Oson; and Chapter XVI, pages 507 to 528: Rice starch: production and uses; by Rohmer and Klem). Devices normally used in processes for extracting starch from plant material are separators, decanters, hydrocyclones, spray dryers and fluidized-bed dryers.

Owing to the expression of a nucleic acid molecule according to the invention, the transgenic plant cells and plants according to the invention synthesize a starch whose physicochemical properties, for example the amylose/amylopectin ratio, the degree of branching, the average chain length, the phosphate content, the gelatinization behavior, the starch granule size and/or starch granule form is altered compared with starch synthesized in wild-type plants. In particular, such a starch may be altered with regard to viscosity and/or the film- or gel-forming properties of gels made from this starch in comparison with known starches.

A further subject matter of the present invention is a starch which is obtainable from the plant cells and plants according to the invention and their propagation material and starch which is obtainable by the above-described process according to the invention.

It is furthermore possible to generate, with the aid of the nucleic acid molecules according to the invention, plant cells and plants in which the activity of a protein according to the invention is reduced. This also leads to the synthesis of a starch with altered chemical and/or physical characteristics compared with starch from wild-type plant cells.

A further subject-matter of the invention is thus also a transgenic plant cell comprising a nucleic acid molecule according to the invention in which the activity of a starch synthase is reduced in comparison with an untransformed cells.

Plant cells with a reduced activity of a starch synthase can be obtained, for example, by expressing a suitable antisense RNA, a sense RNA for achieving a cosuppression effect or by expressing a suitably constructed ribozyme which specifically cleaves transcripts which encode a starch synthase, making use of the nucleic acid molecules according to the invention by methods known to the skilled worker, cf. Jorgensen (Trends Biotechnol. 8 (1990), 340–344), Niebel et al., (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621).

To reduce the activity of a starch synthase according to the invention, it is preferred to reduce, in the plant cells, the number of transcripts encoding it, for example by expressing an antisense RNA.

Here, it is possible to make use, on the one hand, of a DNA molecule which encompasses all of the sequence encoding a protein according to the invention, inclusive of any flanking sequences which may be present, or else of DNA molecules which only encompass parts of the coding sequence, it being necessary for these parts to be sufficiently long so as to cause an antisense effect in the cells. In general, sequences up to a minimum length of 15 bp, preferably with a length of 100–500 bp, may be used, for efficient antisense inhibition, in particular sequences with a length of over 500 bp. As a rule, DNA molecules are used which are shorter than 5000 bp, preferably sequences which are shorter than 2500 bp.

Also possible is the use of DNA sequences which show a high degree of homology, but are not completely identical, with the sequences of the DNA molecules according to the invention. The minimum homology should exceed approx. 65%. The use of sequences with homologies between 95 and 100% is to be preferred.

Another subject matter of the invention is a process for producing a modified starch encompassing the step of extracting the starch from a cell or plant according to the invention and/or from starch-storing parts of such a plant.

A further subject matter of the invention is starch which can be obtained from the cells or plants according to the invention and propagation material, or parts thereof, and also starch which can be obtained by a process according to the invention.

The starches according to the invention can be modified by methods known to the skilled worker and are suitable, in its unmodified or modified form, for a variety of uses in the food or non-food sector.

In principle, the possible uses of the starches according to the invention can be divided into two important sectors. One sector encompasses the hydrolyzates of the starch, mainly glucose and glucan units, which are obtained by enzymatic or chemical methods. They are used as starting material for further chemical modifications and processes such as fermentation. What may be significant for reducing the costs is the simplicity and economic design of a hydrolytic method. It currently proceeds enzymatically using amyloglucosidase. What would be feasible is a financial saving by less use of enzymes. This could be brought about by altering the structure of the starch, for example by increasing the surface area of the granule, easier digestibility, for example owing to a lower degree of branching or a steric structure which limits the accessibility for the enzymes employed.

The other sector in which the starches according to the invention can be used as so-called native starch, owing to their polymeric structure, can be divided into two further fields of application:

1. The Food Industry

Starch is a traditional additive to a large number of foodstuffs in which its function is essentially to bind aqueous additives or to cause increased viscosity or else increased gelling. Important characteristics are the viscoelasticity, the sorptive characteristics, the swelling temperature, the gelatinization temperature, the viscosity, the thickening power, the starch solubility, the transparency and gel structure, the thermal stability, the shear stability, the stability to acids, the tendency to undergo retrogradation, the film-forming capacity, the freeze-thaw-stability, the viscostability in salt solutions, the digestibility and the ability to form complexes with, for example, inorganic or organic ions.

2. The Non-Food Industry

In this important sector, starch can be employed as auxiliary for various preparation processes or as an additive in industrial products. When using the starch as an auxiliary, mention must be made, in particular, of the paper and board industry. Starch acts mainly for retardation purposes (retaining solids), for binding filler particles and fines, as stiffener and for dehydration. Moreover, the advantageous properties of starch regarding stiffness, hardness, sound, touch, luster, smoothness, bonding strength and the surfaces are utilized.

2.1 Paper and Board Industry

Within the papermaking process, four fields of application must be distinguished, i.e. surface, coating, stock and spraying. The demands on starch with regard to surface treatment are essentially high whiteness, an adapted viscosity, high viscostability, good film formation and low dust formation. When used for coating, the solids content, a suitable viscosity, a high binding capacity and a high pigment affinity play an important role. Of importance when used as additive to the stock is rapid, uniform, loss-free distribution, high mechanical strength and complete retention in the paper web. If the starch is used in the spraying sector, again, an adapted solids content, high viscosity and high binding capacity are of importance.

2.2 The Adhesives Industry

An important field of application for starches is the adhesives industry, where the potential uses are divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch-based adhesives are employed in the sectors of production of corrugated board, production of paper sacks and bags, production of composite materials for paper and aluminum, production of box board and gumming adhesives for envelopes, stamps and the like.

2.3 Textile Industry and Textile Care Products Industry

An important field of application for starches as auxiliaries and additives is the sector of production of textiles and textile care products. The following four fields of application must be distinguished within the textile industry: the use of starch as sizing agent, i.e. as auxiliary for smoothing and strengthening the burr behavior as protection from the tensile forces applied during weaving, and for increasing abrasion resistance during weaving, starch as a textile finishing agent, in particular after quality-reducing pretreatments such as bleaching, dyeing and the like, starch as thickener in the preparation of dye pastes for preventing bleeding, and starch as additive to warping agents for sewing threads.

2.4 Construction Materials Industry

The fourth field of application is the use of starches as additives in construction materials. An example is the production of gypsum plasterboards, where the starch which is admixed to the gypsum slurry gelatinizes with the water, diffuses to the surface of the plaster core and there binds the board to the core. Other fields of application are the admixture to rendering and mineral fibers. In the case of ready-mixed concrete, starch products are employed for delaying binding.

2.5 Soil Stabilization

Another market for starch is the production of soil stabilizers, which are employed for the temporary protection of the soil particles from water when the soil is disturbed artificially. According to present knowledge, product combinations of starch and polymer emulsions are to be put on a par with the previously employed products with regard to their erosion- and crust-reducing effect, but are markedly less expensive.

2.6 Use in Crop Protection Products and Fertilizers

One field of application for using starch is in crop protection products for altering the specific properties of the products. Thus, starch can be employed for improving the wetting of crop protection products and fertilizers, for the controlled release of the active ingredients, for converting liquid, volatile and/or malodorous active ingredients into microcrystalline, stable, shapeable substances, for mixing incompatible compounds and for extending the duration of action by reducing decomposition.

2.7 Pharmaceuticals, Medicine and Cosmetics Industry

Another field of application is the sector of the pharmaceuticals, medicine and cosmetics industry. In the pharmaceuticals industry, starch can be employed as binder for tablets or for diluting the binder in capsules. Moreover, starch can be employed as tablet disintegrant since they absorb fluid after swallowing and swell within a short time to such an extent that the active ingredient is liberated. Medicinal lubricating powders and wound powders are starch-based for qualitative reasons. In the cosmetics sector, starches are employed, for example, as carriers of powder additives such as fragrances and salicylic acid. A relatively large field of application for starch is toothpaste.

2.8 Addition of Starch to Charcoal and Briquettes

A field of application for starch is as additive to charcoal and briquette. With an addition of starch, charcoal can be agglomerated, or briquetted, in high quantities, thus preventing early decomposition of the briquettes. In the case of barbecue charcoal, the starch addition amounts to between 4 and 6%, in the case of calorized charcoal to between 0.1 and 0.5%. Moreover, starches are gaining importance as binders since the emission of noxious substances can be markedly reduced when starches are added to charcoal and briquette.

2.9 Ore and Coal Slurry Processing

Furthermore, starch can be employed as flocculant in the ore and coal slurry processing sector.

2.10 Foundry Auxiliary

A further field of application is as additive to foundry auxiliaries. Various casting processes require cores made from sands treated with binders. The binder which is predominantly employed nowadays is bentonite, which is treated with modified starches, in most cases swellable starches.

The purpose of adding starch is to increase flowability and to improve the binding power. In addition, the swellable starches can meet other demands of production engineering, such as being cold-water-dispersible, rehydratable, readily miscible with sand and having high water-binding capacity.

2.11 Use in the Rubber Industry

In the rubber industry, starch can be employed for improving the technical and visual quality. The reasons are the improvement of the surface luster, the improvement of handle and of appearance, and to this end starch is scattered onto the tacky gummed surface of rubber materials prior to cold curing, and also the improvement of the rubber's printability.

2.12 Production of Leather Substitutes

Modified starches may furthermore also be sold for the production of leather substitutes.

2.13 Starch in Synthetic Polymers

In the polymer sector, the following fields of application can be envisaged: the incorporation of starch degradation products in the processing procedure (starch only acts as filler, there is no direct bond between the synthetic polymer and the starch) or, alternatively, the incorporation of starch degradation products in the production of polymers (starch and polymer form a stable bond).

The use of starch as a pure filler is not competitive in comparison with the other substances such as talc. However, this is different when the specific properties of starch make an impact and thus markedly alter the spectrum of characteristics of the end products. An example of this is the use of starch products in the processing of thermoplasts, such as polyethylene. Here, the starch and the synthetic polymer are combined by coexpression in a ratio of 1:1 to give a masterbatch, from which various products are produced with granulated polyethylene, using conventional process techniques. By incorporating starch in polyethylene films, an increased substance permeability in the case of hollow bodies, an improved permeability for water vapor, an improved antistatic behavior, an improved antiblock behavior and an improved printability with aqueous inks can be achieved.

Another possibility is the use of starch in polyurethane foams. By adapting the starch derivatives and by process-engineering optimization, it is possible to control the reaction between synthetic polymers and the starches' hydroxyl groups in a directed manner. This results in polyurethane films which acquire the following spectrum of properties, owing to the use of starch: a reduced thermal expansion coefficient, a reduced shrinking behavior, an improved pressure-tension behavior, an increase in permeability for water vapor without altering the uptake of water, a reduced flammability and a reduced ultimate tensile strength, no drop formation with combustible parts, freedom from halogens, or else reduced aging. Disadvantages which still exist are reduced compressive strength and reduced impact strength.

Product development is currently no longer restricted to films. Solid polymer products such as pots, slabs and dishes which contain a starch content of over 50% may also be produced. Moreover, starch/polymer mixtures are considered advantageous since their biodegradability is much higher.

Starch graft polymers have become exceedingly important owing to their extremely high water-binding capacity. They are products with a starch backbone and a side chain of a synthetic monomer, grafted on following the principle of the free-radical chain mechanism. The starch graft polymers which are currently available are distinguished by a better binding and retention capacity of up to 1000 g of water per g of starch combined with high viscosity. The fields of application of these superabsorbents have extended greatly in recent years and are, in the hygiene sector, products such as diapers and undersheets and, in the agricultural sector, for example in seed coatings.

Decisive for the application of novel, genetically modified starches are, on the one hand, structure, water content, protein content, lipid content, fiber content, ash/phosphate content, amylose/amylopectin ratio, molecular mass distribution, degree of branching, granule size and granule shape and crystallinity, and, on the other hand, also the characteristics which effect the following features: flow and sorption behavior, gelatinization temperature, viscosity, viscostability in salt solutions, thickening power, solubility, gel structure and gel transparency, thermal stability, shear stability, stability to acids, tendency to undergo retrogradation, gel formation, freeze-thaw stability, complex formation, iodine binding, film formation, adhesive power, enzyme stability, digestibility and reactivity.

The production of modified starches by recombinant methods can, on the one hand, alter the properties of the starch derived from the plant in such a way that other modifications by means of chemical or physical processes appear to be no longer required. On the other hand, the starches which have been altered by recombinant methods may be subjected to further chemical modifications, which leads to further improvements in quality for some of the above-described fields of application. These chemical modifications are known in principle. They are, in particular, modifications by thermal treatment, treatment with organic or inorganic acids, oxidation and esterifications, which lead, for example, to the formation of phosphate starches, nitrate starches, sulfate starches, xanthate starches, acetate starches and citrate starches. Moreover, mono- or polyhydric alcohols in the presence of strong acids may be employed for producing starch ethers, resulting in starch alkyl ethers, O-allyl ethers, hydroxyalkyl ethers, O-carboxymethyl ethers, N-containing starch ethers, P-containing starch ethers), S-containing starch ethers, crosslinked starches or starch graft polymers.

A preferred use of the starches according to the invention is the production of packaging materials and disposable articles, on the one hand, and as foodstuff or foodstuff precursor on the other hand.

To express the nucleic acid molecules according to the invention in sense or antisense orientation in plant cells, they are linked to regulatory DNA elements which ensure transcription in plant cells. These include, in particular, promoters, enhancers and terminators. In general, any promoter which is active in plant cells is suitable for expression.

The promoter may be chosen in such a way that expression is constitutive or takes place only in a particular tissue, at a particular point in time of plant development or at a point in time determined by external factors. Relative to the plant, the promoter can be homologous or heterologous. Examples of suitable promoters are the cauliflower mosaic virus 35S RNA promoter and the maize ubiquitin promoter for constitutive expression, the patatin promoter B33 (Rocha-Sosa et al., EMBO J. 8 (1989), 23–29) for tuber-specific expression, or a promoter which ensures expression only in photosynthetically active tissues, for example the ST-LS1 promoter (Stockhaus et al., Proc. Natl. Acad. Sci. USA 84 (1987), 7943–7947; Stockhaus et al., EMBO J. 8 (1989), 2445–2451) or, for endosperm-specific expression, the wheat HMG promoter, the USP promoter, the phaseolin promoter or promoters from maize zein genes.

A termination sequence which serves to correctly terminate transcription and to add a poly-A tail to the transcript, which is considered to have a function in stabilizing the transcript, may also be present. Such elements have been described in the literature (cf. Gielen et al., EMBO J. 8 (1989), 23–29) and are exchangeable as desired.

The present invention provides nucleic acid molecules which encode a protein with a soluble wheat starch synthase function. The nucleic acid molecules according to the invention permit the production of this enzyme whose functional identification in starch biosynthesis, the generation of plants which have been altered by recombinant technology in which the activity of this enzyme is altered and thus allows a starch to be synthesized whose structure is altered and whose physicochemical properties are altered.

In principle, the nucleic acid molecules according to the invention may also be used for generating plants in which the activity of the starch synthase according to the invention is increased or reduced while simultaneously the activities of other enzymes which participate in starch synthesis are altered. Altering the activities of a starch synthase in plants results in the synthesis of a starch with altered structure. Furthermore, nucleic acid molecules which encode a starch synthase, or suitable antisense constructs can be introduced into plant cells in which the synthesis of endogenous GBSS I, SSS or GBSS II proteins is already inhibited on account of an antisense effect or a mutation, or the synthesis of the branching enzyme is already inhibited (as, for example, in WO 92/14827 or Shannon and Garwood, 1984, in Whistler, BeMiller and Paschall, Starch: Chemistry and Technology, Academic Press, London, 2nd Edition: 25–86).

If it is intended to achieve the inhibition of the synthesis of several enzymes involved in starch biosynthesis in transformed plants, the transformation may involve DNA molecules which simultaneously comprise several regions encoding the enzymes in question in antisense orientation under the control of a suitable promoter. Here, it is possible as an alternative for each sequence to be under the control of its own promoter, or the sequences can be transcribed as fusion from a joint promoter or be under the control of a joint promoter. The last-mentioned alternative will generally be preferred, since in this case the synthesis of the proteins in question should be inhibited roughly to the same extent. As regards the length of the individual coding regions used in such a construct, what has been mentioned above for the generation of antisense constructs also applies here. In principle, there is no upper limit for the number of antisense fragments transcribed in such a DNA molecule starting from one promoter. However, the transcript formed should preferably not exceed a length of 10 kb, in particular a length of 5 kb.

Coding regions localized in such DNA molecules in combination with other coding regions in antisense orientation behind a suitable promoter may be derived from DNA sequences which encode the following proteins: starch-granule bound starch synthases (GBSS I and II) and soluble starch synthases (SSS I and II), branching enzymes (isoamylases, pullulanases, R-enzymes, branching enzymes, debranching enzymes), starch phosphorylases and disproportioning enzymes. This enumeration is only by way of example. The use of other DNA sequences for the purposes of such a combination is also feasible.

Such constructs allow the synthesis of a plurality of enzymes to be inhibited simultaneously in plant cells transformed with said constructs.

Furthermore, the constructs can be introduced into plant mutants which are deficient for one or more starch biosynthesis genes (Shannon and Garwood, 1984, in Whistler, BeMiller and Paschall, Starch: Chemistry and Technology, Academic Press, London, 2nd Edition: 25–86). These defects may relate to the following proteins: starch-granule-bound starch synthases (GBSS I and II) and soluble starch synthases (SSS I and II), branching enzymes (BE I and II), debranching enzymes (R-enzymes), disproportioning enzymes and starch phosphorylases. This enumeration is only by way of example.

Such a procedure furthermore allows the synthesis of a plurality of enzymes to be inhibited simultaneously in plant cells transformed with them.

To prepare the introduction of foreign genes into higher plants, a large number of cloning vectors containing a replication signal for *E. coli* and a marker gene for selecting transformed bacterial cells are available. Examples of such vectors are pBR322, pUC series, M13 mp series, pACYC184 and the like. The desired sequence may be introduced into the vector at a suitable restriction cleavage site. The plasmid obtained is used to transform *E. coli* cells. Transformed *E. coli* cells are grown in a suitable medium and subsequently harvested and lyzed. The plasmid is recovered. Analytical methods for characterizing the plasmid DNA obtained which are generally used are restriction analyses, gel electrophoresis and further methods of biochemistry and molecular biology. After each manipulation, the plasmid DNA can be cleaved and resulting DNA fragments linked to other DNA sequences. Each plasmid DNA sequence can be cloned in the same or different plasmids.

A large number of techniques are available for introducing DNA into a plant host cell. These techniques encompass the transformation of plant cells with T-DNA using *Agrobacterium tumefaciens* or *Agrobacterium rhizogenes* as transformation agents, protoplast fusion, injection, the electroporation of DNA, the introduction of DNA by means of the biolistic method, and other possibilities.

The injection and electroporation of DNA into plant cells make no particular demands on the plasmids used. Simple plasmids such as, for example, pUC derivatives may be used. However, if intact plants are to be regenerated from cells transformed in this way, the presence of a selectable marker gene is required.

Depending on the method of introducing desired genes into the plant cell, further DNA sequences may be required. If, for example, the Ti or Ri plasmid is used for transforming the plant cell, at least the right border, but frequently the right and left border, of the Ti and Ri plasmid T-DNA must be linked to the genes to be introduced as flanking region.

If *agrobacteria* are used for the transformation, the DNA to be introduced must be cloned into specific plasmids, either into an intermediate vector or into a binary vector. The intermediate vectors can be integrated into the agrobacterial Ti or Ri plasmid by homologous recombination owing to sequences which are homologous to sequences in the T-DNA. Said plasmid also contains the vir region, which is required for the T-DNA transfer. Intermediate vectors cannot replicate in *agrobacteria*. The intermediate vector can be transferred to *Agrobacterium tumefaciens* by means of a helper plasmid (conjugation). Binary vectors are capable of replication in *E. coli* and in *agrobacteria*. They contain a selection marker gene and a linker or polylinker, which are framed by the right and left T-DNA border region. They can be transformed directly into the *agrobacteria* (Holsters et al. Mol. Gen. Genet. 163 (1978), 181–187). The *agrobacterium* which acts as the host cell should contain a plasmid carrying a vir region. The vir region is required for transferring the T-DNA into the plant cell. Additional T-DNA may be present. The *agrobacterium* thus transformed can be used for transforming plant cells.

The use of T-DNA for transforming plant cells has been researched intensively and been described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 146 and An et al. EMBO J. 4 (1985), 277–287.

To transfer the DNA into the plant cell, plant explants can expediently be cocultured with *Agrobacterium tumefaciens* or *Agrobacterium rhizogenes*. Intact plants can then be regenerated from the infected plant material (for example leaf sections, stalk sections, roots, but also protoplasts, or plant cells grown in suspension culture) in a suitable medium which can contain, inter alia, certain sugars, amino acids, antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L., 1993 Transgenic plants. In: Biotechnology, A Multi-Volume Comprehensive Treatise (H. J. Rehm, G. Reed, A. Püuhler, P. Stadler, eds.), Vol. 2, 627–659, VCH Weinheim-New York-Basel-Cambridge).

While the transformation of dicotyledonous plants via Ti-plasmid vector systems with the aid of *Agrobacterium tumefaciens* is well established, more recent work suggests that even monocotyledonous plants are indeed accessible to transformation by means of *agrobacterium*-based vectors (Chan et al., Plant Mol. Biol. 22 (1993), 491–506; Hiei et al., Plant J. 6 (1994), 271–282).

Alternative methods for the transformation of monocotyledonous plants are the transformation by means of the biolistic approach, protoplast transformation, or the physically or chemically induced DNA uptake into protoplasts, for example by electroporation of partially permeabilized cells, transfer of DNA by means of glass fibers, macroinjection of DNA into inflorescences, the microinjection of DNA into microspores or proembryos, DNA uptake by germinating pollen and DNA uptake in embryos by swelling (review: Potrykus, Physiol. Plant (1990), 269–273).

Three of the abovementioned transformation systems have been established in the past for various cereals: the electroporation of tissue, the transformation of protoplasts and the DNA transfer by particle bombardment into regenerable tissue and cells (review: Jähne et al., Euphytica 85 (1995), 35–44).

Different methods of transforming wheat have been described in the literature (review: Maheshwari et al., Critical Reviews in Plant Science 14 (2) (1995), 149 to 178): Hess et al. (Plant Sci. 72 (1990), 233) employed the macroinjection method to bring pollen and *agrobacteria* into immediate vicinity. The mobilization of the plasmid which contained the nptII gene as selectable marker was detected by Southern blot analysis and NPTII test. The transformants showed a normal phenotype and were fertile. Kanamycin resistance was detected in two consecutive generations.

The first transgenic fertile wheat plant which was regenerated after bombardment with DNA bound to microprojectiles was described by Vasil et al. (Bio/Technology 10 (1992), 667–674). The target tissue for the bombardment was an embryogenic callus culture (type C callus). The selection marker employed was the bar gene which encodes a phosphinothricin acetyltransferase and thus mediates resistance to the herbicide phosphinothricin. A further system was described by Weeks et al. (Plant Physiol. 102 (1993), 1077–1084), and Becker et al. (Plant J. 5(2) (1994), 299–307). Here, the target tissue for the DNA transformation is the scutellum of immature embryos which was stimulated in a preliminary in-vitro phase to induce somatic embryos. The transformation efficacy in the system developed by Becker et al. (loc cit.) is 1 transgenic plant per 83 embryos of the variety "Florida" and thus markedly higher than the system established by Weeks et al., which yields 1 to 2 transgenic plants per 1000 embryos of the variety "Bohwhite".

The system developed by Becker et al. (loc cit.) forms the basis for the transformation experiments described in the examples.

Once the DNA introduced is integrated into the genome of the plant cell, it is, as a rule, stable there and is also retained in the progeny of the originally transformed cell. It normally contains one of the above-mentioned selection markers which mediates resistance to a biocide such as phosphinothricin or an antibiotic such as kanamycin, G 418, bleomycin or hygromycin, to the transformed plant cells or which permits selection via the presence or absence of certain sugars or amino acids. The marker chosen individually should therefore allow the selection of transformed cells over cells which lack the DNA introduced.

Within the plant, the transformed cells grow in the customary manner (see also McCormick et al., Plant Cell Reports 5 (1986), 81–84). The resulting plants can be grown normally and hybridized with plants which have the same transformed germ plasm or other germ plasms. The resulting hybrid individuals have the corresponding phenotype properties. Seeds may be obtained from the plant cells.

Two or more generations should be grown in order to ensure that the phenotype characteristic is stably retained and inherited. Also, seeds should be harvested in order to ensure that the phenotype in question or other properties have been retained.

The examples which follow are intended to illustrate the invention and constitute no restriction whatsoever.

1. Cloning Methods

The vector pBluescript II SK (Stratagene) was used for cloning in *E. coli*.

2. Bacterial Strains

The *E. coli* strain DH5α (Bethesda Research Laboratories, Gaithersburg, USA) was used for the Bluescript vector and for the antisense constructs. The *E. coli* strain XL1-Blue was used for the in-vivo excision.

3. Transformation of Immature Wheat Embryos

| Media | | |
|---|---|---|
| MS: | 100 ml/l macrosalt<br>1 ml/l microsalt<br>2 ml/l Fe/NaEDTA<br>30 g/l sucrose | (D. Becker and H. Lörz,<br>Plant Tissue Culture<br>Manual (1996), B 12:1–20) |
| #30: | MS + 2,4-D (2 mg/l) | |
| #31: | MS + 2,4-D (2 mg/l) + phosphinothricin (PPT active component of herbicide BASTA (2 mg/l)) | |
| #32: | MS + 2,4-D (0.1 mg/l) + PPT (2 mg/l) | |
| #39: | MS + 2,4-D (2 mg/l) + of each 0.5 N mannitol/sorbitol | |

The media stated were brought to pH 5.6 using KOH and solidified using 0.3% Gelrite.

The method for transforming in mature wheat embryos was developed and optimized by Becker and Lörz (D. Becker and H. Lörz Plant Tissue Culture Manual (1996), B12: 1 to 20).

In the experiments described hereinbelow, the procedure developed by Becker and Lörz (loc. cit.) was adhered to.

For the transformation, ears with caryopses of developmental stage 12 to 14 days after anthesis were harvested and surface-sterilized. The isolated scutella were plated onto induction medium #30 with the embryo axis orientated towards the medium.

After preculture for 2 to 4 days (26° C., in darkness), the explants are transferred to medium #39 for the osmotic preculture (2 to 4 h, 26° C., in the dark).

For the biolistic transformation, approx. 29 μg of gold parts onto which a few μg of the target DNA had previously been precipitated were employed per shot. Since the experiments carried out are cotransformations, the target DNA added to the precipitation batch is composed of the target gene and a resistance marker gene (bar gene) in the ratio 1:1.

4. DIG Labeling of DNA Fragments

DNA fragments employed as screening probes were labeled via a specific PCR with the incorporation of DIG-labeled dUTP (Boehringer Mannheim, Germany).

Media solutions used in me examples:

20×SSC 175.3 g NaCl 88.2 g sodium citrate twice-distilled H2O to 1000 ml

10 N NaOH to pH 7.0

Plasmid pTaSSI 8/1 was deposited at the DSMZ in Braunschweig, Federal Republic of Germany, as specified in the Budapest Treaty under the No. DSM 12794.

EXAMPLE 1

Identification, Isolation and Characterization of a cDNA Encoding a Soluble Wheat Starch Synthase (SS II) (*Triticum Aestivum* L., cv Florida).

To identify the complete cDNA which encodes an isoform of a soluble wheat starch synthase (SS I), the heterologous screening strategy was followed. To this end, a wheat cDNA library was screened with suitable oligonucleotides. The SS I specific oligonucleotide which was employed in the screening had been isolated as described hereinbelow using the 5'RACE method (Rapid Amplification of cDNA ends).

The wheat cDNA library was synthesized from poly(A)+ RNA of approx. 20-day-old caryopses (endosperm) in a Lambda Zap II vector following the manufacturer's instructions (Lambda ZAP II-cDNA Synthesis Kit, Stratagene GmbH, Heidelberg, Germany). After determination of the titer of the cDNA library, a primary titer of $1.26 \times 10^6$ pfu/ml was determined.

The cDNA library was screened with an SS I probe from wheat. Using 5'-RACE, a DNA fragment was isolated and the 5' end was amplified with a 5'RACE kit (hereinbelow termed "kit") by Boehringer (Mannheim, Germany). All steps were carried out following the manufacture's instructions. Unless otherwise described, only reagents and enzymes from the kit were used.

First, poly(A)+ RNA of approx. 20-day-old caryopses was transcribed into single-stranded cDNA and employed in a tailing reaction. The resulting cDNA, which was provided in the 5' region with the oligo(dA)anchor#9 (kit) was amplified in a first reaction with the primers oligo(dT)#8 (kit) and B2F5 following a modified protocol, as follows: in a 50 μl batch, 5 μl of tailed cDNA, 5 μl of 10× reaction buffer (Life Technologies), 0.25 μM B2F5 primer, 0.75 μM oligo(dT)#8, 0.2 mM dNTPs and 5U Taq polymerase (recombinant, Life Technologies) were employed. The PCR profile was: 94° C. 3 min/94° C. 45 sec/56° C. 1 min/72° C. 1 min 30 sec, 29 cycles/72° C. 5 min.

Thereupon, a further PCR was carried out with the primers oligo(dT)#8 (kit), B2F5 and the primer B2F6, which was positioned at 5'. In a 50 μl batch, 1 μl of PCR product, 5 μl of 10× reaction buffer (Life Technologies), 0.25 μM B2F5 primer, 0.25 μM B2F6 primer, 0.75 μM oligo(dT)#8, 0.2 mM dNTPs and 5U Taq polymerase (recombinant, Life Technologies) were employed. The PCR profile was:

94° C. 3 min/94° C. 45 sec/60° C. 1 min/72° C. 1 min 30 sec; 29 cycles/72° C. 5 min B2F5: 5'CCTCCCAATTCAAGGATTAGTG 3' (Seq ID NO. 3)

B2F6: 5'CCTCGCATGCAGCATAGCAA 3' (Seq ID NO. 4)

The PCR products obtained by the above methods were separated in an agarose gel and the DNA fragments with a size of above 800 bp was isolated. The PCR fragments were cloned using the pCR-Script SK(+) Cloning Kit by Stratagene (Heidelberg). Sequence analysis of the cloned subfragments allowed approx. 150 bp of as yet unknown sequence of the SS I clone to be identified.

The oligonucleotides B2R00 and B2F6.2 were selected from the 5'-region of this novel sequence to amplify a DNA fragment (SS I probe) which was subsequently labeled with digoxygenin-11-dUTP as described and used as probe for screening the wheat cDNA library. The SS I probe was labeled by means of a PCR reaction with the primers B2R00 and B2F6.2 following the instructions in "The DIG System User's Guide for Filter Hybridisation" (Boehringer Mannheim).

B2R00: 5'TGTGGCTGCAAGTGAGGAGG 3' (Seq ID NO. 5)

B2F6.2 5'CCAGTCACAAACACGTAGCTACG 3' (Seq ID NO. 6)

To screen the wheat cDNA library, approx. 700 000 phages were plated. The phages were plated and the plates blotted following standard protocols. The filters were pre-hybridized and hybridized in 5×SSC, 3% Blocking (Boehringer Mannheim), 0.2% sodium dodecyl sulfate (SDS), 0.1% sodium laurylsarcosine and 50 μg/ml herring sperm DNA at 65° C. 1.3 ng/ml of the DIG-labeled SS I probe were added to the hybridization solution and the hybridization was incubated overnight. The filters were washed as described in the protocol in "The DIG System User's Guide for Filter Hybridisation" (Boehringer Mannheim) at 65° C. Positive clones were singled out by 2 further screening cycles. Single clones were obtained via in-vivo excision as pBluescript SK phagemids (procedure following the manufacture's instructions; Stratagene, Heidelberg).

After the clones had been analyzed via minipreps and after the plasmid DNA had been restricted, clone TaSSI 8/1 was analyzed further.

EXAMPLE 2

Sequence Analysis of the cDNA Insertions of Plasmid pTaSSI 8/1

The plasmid DNA was isolated from clone pTaSSI 8/1 and the sequence of the cDNA insertions determined by means of the dideoxynucleotide method (Sanger et al., Proc. Natl. Acad. Sci. USA 74 (1977), 5463–5467). The insertion of clone TaSSI 8/1 is 2805 bp in length and constitutes complete cDNA. The nucleotide sequence is shown in Seq ID NO. 1. The corresponding amino acid sequence is shown in Seq ID NO. 2. A comparison with already published sequences revealed that the sequence shown under Seq ID NO. 1 is novel and comprises a complete coding region.

EXAMPLE 3

Generation of the Plant Transformation Vector pTa-gamma-SSI-8/1

To express the cDNA isolated in Example 1, the plant transformation vector pTa-gamma-SSI-8/1 was constructed based on pUC19 as basal plasmid. To construct the vector, the cDNA insertion of plasmid TaSSI 8/1 is linked completely in sense orientation to the 3'-end of the ubiquitin promoter. This promoter is composed of the first untranslated exon and the first intron of the maize ubiquitin 1 gene (Christensen A. H. et al., Plant Molecular Biology 18 (1992), 675–689). Parts of the polylinker and the NOS terminator are derived from plasmid pACT1.cas (CAMBIA, TG 0063; Cambia, GPO Box 3200, Canberra ACT 2601, Australia). Vector constructs with this terminator and constructs based on pAct1.cas are described by McElroy et al. (Molecular Breeding 1 (1995), 27–37). The resulting vector was termed pUbi.cas.

The expression vector was cloned by restricting a fragment from clone TaSSI 8/1 with the restriction enzymes Xba I and Ssp I. The ends of the fragment were filled in by means of a Klenow reaction and the fragment was subsequently ligated into the Sma I cloning site of the expression vector pUbi.cas. The resulting expression vector was termed pTA-gamma-SSI 8.1. In a second construct, the 5'-untranslated leader of clone TaSSI-8.1 was first removed by exonuclease treatment. It was then cloned into the expression vector pUbi.cas. This construct was termed Ta-gamma-SSI-8/1-2.

To the vectors pTa-gamma-SSI-8/1 and pTa-gamma-SSI-8/1-2 are subsequently used for transforming wheat.

What is claimed is:

1. An isolated nucleic acid molecule encoding a protein with the function of a wheat starch synthase, selected from the group consisting of
   (a) a nucleic acid molecule encoding a protein having the amino acid sequence of SEQ ID NO:2,
   (b) a nucleic acid molecule having the nucleotide sequence of SEQ ID NO:1 or a ribonucleotide sequence corresponding therewith;
   (c) a nucleic acid molecule whose nucleotide sequence deviates from the sequence of a nucleic acid molecule mentioned under (a) or (b) owing to the degeneracy of the genetic code.

2. The nucleic acid molecule as claimed in claim 1, which is a DNA molecule.

3. The DNA molecule as claimed in claim 2, which is a cDNA molecule.

4. The nucleic acid molecule as claimed in claim 1, comprising regulatory elements.

5. The nucleic acid molecule as claimed in claim 1, which is an RNA molecule.

6. A vector containing the isolated nucleic acid molecule as claimed in claim 1.

7. The vector as claimed in claim 6, wherein said nucleic acid molecule is operably linked in sense orientation to regulatory elements which ensure transcription and synthesis of a translatable RNA in prokaryotic or eukaryotic cells.

8. The vector as claimed in claim 6, wherein said nucleic acid molecule is operably linked in sense orientation with respect to regulatory elements, and wherein a cosuppression effect is achieved in prokaryotic or eukaryotic cells.

9. The vector as claimed in claim 6, wherein said nucleic acid molecule is operably linked in antisense orientation with respect to regulatory elements which ensure the synthesis of an untranslatable RNA in prokaryotic or eukaryotic cells.

10. A host cell comprising the nucleic acid molecule as claimed in claim 1 or the vector as claimed in claim 6.

11. A process for the preparation of a protein encoded by the nucleic acid molecule as claimed in claim 1, wherein the host cell as claimed in claim 10 is cultured under conditions which permit said protein to be synthesized,
    and said protein is isolated from cultured host cells or culture medium, or both.

12. A process for generating a transgenic plant cell, wherein
  (a) the nucleic acid molecule as claimed in claim 1 or
  (b) the vector as claimed in claim 6
is integrated into the genome of a plant cell.

13. A transgenic plant cell comprising the nucleic acid molecule as claimed in claim 1 or the vector as claimed in claim 6.

* * * * *

SEQUENCE LISTING

```
<160> NUMBER OF SEQ ID NOS: 6

<210> SEQ ID NO 1
<211> LENGTH: 2771
<212> TYPE: DNA
<213> ORGANISM: Triticum aestivum
<220> FEATURE:
<221> NAME/KEY: CDS
<222> LOCATION: (280)..(2547)

<400> SEQUENCE: 1
cgccactcca ctcgccttgc cccactccca ctcttctctc cccgcgcaca ccgagtcggc     60
accggctcat cacccatcac ctcggcctcg gccaccggca aaccccccga tccgcttttg    120
caggcagcgc actaaaaccc cggggagcgc gccccgcggc agcagcagca ccgcagtggg    180
agagagaggc ttcgccccgg cccgcaccga gcggggcgat ccaccgtccg tgcgtccgca    240
cctcctccgc ctcctcccct gtcccgcgcg cccacaccc atg gcg gcg acg ggc       294
                                          Met Ala Ala Thr Gly
                                          1               5 gtc ggc gcc ggg tgc ctc gcc ccc agc gtc cgc ctg cgc gcc gat ccg      342
Val Gly Ala Gly Cys Leu Ala Pro Ser Val Arg Leu Arg Ala Asp Pro
                10                  15                  20 gcg acg gcg gcc cgg gcg tcc gcc tgc gtc gtc cgc gcg cgg ctc cgg      390
Ala Thr Ala Ala Arg Ala Ser Ala Cys Val Val Arg Ala Arg Leu Arg
            25                  30                  35 cgc ttg gcg cgg ggc cgc tac gtc gcc gag ctc agc agg gag ggc ccc      438
Arg Leu Ala Arg Gly Arg Tyr Val Ala Glu Leu Ser Arg Glu Gly Pro
        40                  45                  50 gcg gcg cgc ccc gcg cag cag cag caa ctg gcc ccg ccg ctc gtg cca      486
Ala Ala Arg Pro Ala Gln Gln Gln Gln Leu Ala Pro Pro Leu Val Pro
    55                  60                  65 ggc ttc ctc gcg ccg ccg ccg ccc gcg ccc gcc cag tcg ccg gcc ccg      534
Gly Phe Leu Ala Pro Pro Pro Pro Ala Pro Ala Gln Ser Pro Ala Pro
70                  75                  80                  85 acg cag ccg ccc ctg ccg gac gcc ggc gtg ggg gaa ctc gcg ccc gac      582
Thr Gln Pro Pro Leu Pro Asp Ala Gly Val Gly Glu Leu Ala Pro Asp
                90                  95                  100 ctc ctg ctc gaa ggg att gct gag gat tcc atc gac agc ata att gtg      630
Leu Leu Leu Glu Gly Ile Ala Glu Asp Ser Ile Asp Ser Ile Ile Val
            105                 110                 115 gct gca agt gag cag gat tct gag atc atg gat gcg aat gag caa cct      678
Ala Ala Ser Glu Gln Asp Ser Glu Ile Met Asp Ala Asn Glu Gln Pro
        120                 125                 130 caa gct aaa gtt aca cgt agc atc gtg ttt gtg act ggt gaa gct gct      726
Gln Ala Lys Val Thr Arg Ser Ile Val Phe Val Thr Gly Glu Ala Ala
    135                 140                 145
```

-continued

| | | |
|---|---|---|
| cct tat gca aag tca ggg ggg ttg gga gat gtt tgt ggt tcg tta cca<br>Pro Tyr Ala Lys Ser Gly Gly Leu Gly Asp Val Cys Gly Ser Leu Pro<br>150               155                   160               165 | 774 |
| att gct ctt gct gct cgt ggt cac cga gtg atg gtt gta atg cca aga<br>Ile Ala Leu Ala Ala Arg Gly His Arg Val Met Val Val Met Pro Arg<br>              170                   175                   180 | 822 |
| tac tta aat ggg tcc tct gat aaa aac tat gca aag gca tta tac act<br>Tyr Leu Asn Gly Ser Ser Asp Lys Asn Tyr Ala Lys Ala Leu Tyr Thr<br>                   185                   190               195 | 870 |
| gcg aag cac att aag att cca tgc ttt ggg gga tca cat gaa gtg acc<br>Ala Lys His Ile Lys Ile Pro Cys Phe Gly Gly Ser His Glu Val Thr<br>200               205                   210 | 918 |
| ttt ttt cat gag tat aga gac aac gtc gat tgg gtg ttt gtc gat cat<br>Phe Phe His Glu Tyr Arg Asp Asn Val Asp Trp Val Phe Val Asp His<br>             215                   220              225 | 966 |
| ccg tca tat cac aga cca gga agt tta tat gga gat aat ttt ggt gct<br>Pro Ser Tyr His Arg Pro Gly Ser Leu Tyr Gly Asp Asn Phe Gly Ala<br>230               235                   240              245 | 1014 |
| ttt ggt gat aat cag ttc aga tac aca ctc ctt tgc tat gct gca tgc<br>Phe Gly Asp Asn Gln Phe Arg Tyr Thr Leu Leu Cys Tyr Ala Ala Cys<br>                   250                   255               260 | 1062 |
| gag gcc cca cta atc ctt gaa ttg gga gga tat att tat gga cag aat<br>Glu Ala Pro Leu Ile Leu Glu Leu Gly Gly Tyr Ile Tyr Gly Gln Asn<br>             265                   270              275 | 1110 |
| tgc atg ttt gtt gtg aac gat tgg cat gcc agc ctt gtg cca gtc ctt<br>Cys Met Phe Val Val Asn Asp Trp His Ala Ser Leu Val Pro Val Leu<br>                 280                   285              290 | 1158 |
| ctt gct gca aaa tat aga cca tac ggt gtt tac aga gat tcc cgc agc<br>Leu Ala Ala Lys Tyr Arg Pro Tyr Gly Val Tyr Arg Asp Ser Arg Ser<br>295               300                   305 | 1206 |
| acc ctt gtt ata cat aat tta gca cat cag ggt gtg gag cct gca agt<br>Thr Leu Val Ile His Asn Leu Ala His Gln Gly Val Glu Pro Ala Ser<br>310               315                   320              325 | 1254 |
| aca tat cct gat ctg gga ttg cct cct gaa tgg tat gga gct tta gaa<br>Thr Tyr Pro Asp Leu Gly Leu Pro Pro Glu Trp Tyr Gly Ala Leu Glu<br>                   330                   335              340 | 1302 |
| tgg gta ttt cca gaa tgg gca agg agg cat gcc ctt gac aag ggt gag<br>Trp Val Phe Pro Glu Trp Ala Arg Arg His Ala Leu Asp Lys Gly Glu<br>             345                   350              355 | 1350 |
| gca gtt aac ttt ttg aaa gga gca gtt gtg aca gca gat cgg att gtg<br>Ala Val Asn Phe Leu Lys Gly Ala Val Val Thr Ala Asp Arg Ile Val<br>                 360                   365              370 | 1398 |
| acc gtc agt cag ggt tat tca tgg gag gtc aca act gct gaa ggt gga<br>Thr Val Ser Gln Gly Tyr Ser Trp Glu Val Thr Thr Ala Glu Gly Gly<br>375               380                   385 | 1446 |
| cag ggc ctc aat gag ctc tta agc tcc cga aaa agt gta ttg aat gga<br>Gln Gly Leu Asn Glu Leu Leu Ser Ser Arg Lys Ser Val Leu Asn Gly<br>390               395                   400              405 | 1494 |
| att gta aat gga att gac att aat gat tgg aac ccc acc aca gac aag<br>Ile Val Asn Gly Ile Asp Ile Asn Asp Trp Asn Pro Thr Thr Asp Lys<br>                 410                   415              420 | 1542 |
| tgt ctc cct cat cat tat tct gtc gat gac ctc tct gga aag gcc aaa<br>Cys Leu Pro His His Tyr Ser Val Asp Asp Leu Ser Gly Lys Ala Lys<br>             425                   430              435 | 1590 |
| tgt aaa gct gaa ttg cag aag gag ttg ggt tta cct gta agg gag gat<br>Cys Lys Ala Glu Leu Gln Lys Glu Leu Gly Leu Pro Val Arg Glu Asp<br>440               445                   450 | 1638 |
| gtt cct ctg att ggc ttt att gga aga ctg gat tac cag aaa ggc att<br>Val Pro Leu Ile Gly Phe Ile Gly Arg Leu Asp Tyr Gln Lys Gly Ile<br>455               460                   465 | 1686 |

```
gat ctc att aaa atg gcc att cca gag ctc atg agg gag gac gtg caa    1734
Asp Leu Ile Lys Met Ala Ile Pro Glu Leu Met Arg Glu Asp Val Gln
470                 475                 480                 485 ttt gtc atg ctt gga tct ggg gat cca att ttt gaa ggc tgg atg aga    1782
Phe Val Met Leu Gly Ser Gly Asp Pro Ile Phe Glu Gly Trp Met Arg
                490                 495                 500 tct acc gag tcg agt tac aag gat aaa ttc cgt gga tgg gtt gga ttt    1830
Ser Thr Glu Ser Ser Tyr Lys Asp Lys Phe Arg Gly Trp Val Gly Phe
            505                 510                 515 agt gtt cca gtt tcc cac aga ata act gca ggt tgc gat ata ttg tta    1878
Ser Val Pro Val Ser His Arg Ile Thr Ala Gly Cys Asp Ile Leu Leu
        520                 525                 530 atg cca tcg aga ttt gaa cct tgc ggt ctt aat cag cta tat gct atg    1926
Met Pro Ser Arg Phe Glu Pro Cys Gly Leu Asn Gln Leu Tyr Ala Met
    535                 540                 545 caa tat ggt aca gtt cct gta gtt cat gga act ggg ggc ctc cga gac    1974
Gln Tyr Gly Thr Val Pro Val Val His Gly Thr Gly Gly Leu Arg Asp
550                 555                 560                 565 aca gtc gag acc ttc aac cct ttt ggt gca aaa gga gag gag ggt aca    2022
Thr Val Glu Thr Phe Asn Pro Phe Gly Ala Lys Gly Glu Glu Gly Thr
                570                 575                 580 ggg tgg gcg ttc tca ccg cta acc gtg gac aag atg ttg tgg gca ttg    2070
Gly Trp Ala Phe Ser Pro Leu Thr Val Asp Lys Met Leu Trp Ala Leu
            585                 590                 595 cga acc gcg atg tcg aca ttc agg gag cac aag ccg tcc tgg gag ggg    2118
Arg Thr Ala Met Ser Thr Phe Arg Glu His Lys Pro Ser Trp Glu Gly
        600                 605                 610 ctc atg aag cga ggc atg acg aaa gac cat acg tgg gac cat gcc ccg    2166
Leu Met Lys Arg Gly Met Thr Lys Asp His Thr Trp Asp His Ala Pro
    615                 620                 625 agc agt acg agc aga tct tcg agt ggg cct tcg tgg acc aac cct acg    2214
Ser Ser Thr Ser Arg Ser Ser Ser Gly Pro Ser Trp Thr Asn Pro Thr
630                 635                 640                 645 tca tgt aga cgg gga ctg ggg agg tcc aag tgc gag tct cct tca gct    2262
Ser Cys Arg Arg Gly Leu Gly Arg Ser Lys Cys Glu Ser Pro Ser Ala
                650                 655                 660 ctg aag aca tcc tct tca tcc ttc cgc ggc ccg gaa gga tac ccc tgt    2310
Leu Lys Thr Ser Ser Ser Ser Phe Arg Gly Pro Glu Gly Tyr Pro Cys
            665                 670                 675 aca ttg cgt tgt cct gct aca gta gag tcg caa tgc gcc tgc ttg ctt    2358
Thr Leu Arg Cys Pro Ala Thr Val Glu Ser Gln Cys Ala Cys Leu Leu
        680                 685                 690 tgg ttc gcc ggt tcg aga aca tat gac ggc tgt gct gct gcg gcg gtg    2406
Trp Phe Ala Gly Ser Arg Thr Tyr Asp Gly Cys Ala Ala Ala Ala Val
    695                 700                 705 aca gct tcg ggt gga cga cag tta cag ttt tgg gga ata agg aag gga    2454
Thr Ala Ser Gly Gly Arg Gln Leu Gln Phe Trp Gly Ile Arg Lys Gly
710                 715                 720                 725 tgt gct gca gga tgg tta aca gca aag cac cac tca gat ggc agc ctc    2502
Cys Ala Ala Gly Trp Leu Thr Ala Lys His His Ser Asp Gly Ser Leu
                730                 735                 740 tct gtc cgt gtt aca gct gaa atc aga aac caa ctg gtg act ctt        2547
Ser Val Arg Val Thr Ala Glu Ile Arg Asn Gln Leu Val Thr Leu
            745                 750                 755 tagccttagt gattgtgaag tttgttgcct tctgtgtatg ttgtcttgtc cttagctgac    2607
aaatatttga cctgttggag aatttttatct ttgctgctgt ttttttttaa tcaaaagagg    2667
gggtttcctc cgatttcatt aaaaaaaaaa aaaaaaaaaa aaaaaaaaaa aaaaaaaaaa    2727
```
aaaaaaaaaa aaaaaaaaaa aaaaaaaaaa aaaaaaaaaa aaaa    2771

<210> SEQ ID NO 2
<211> LENGTH: 756
<212> TYPE: PRT
<213> ORGANISM: Triticum aestivum

<400> SEQUENCE: 2

Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
            20                  25                  30

Arg Ala Arg Leu Arg Arg Leu Ala Arg Gly Arg Tyr Val Ala Glu Leu
        35                  40                  45

Ser Arg Glu Gly Pro Ala Ala Arg Pro Ala Gln Gln Gln Leu Ala
50                  55                  60

Pro Pro Leu Val Pro Gly Phe Leu Ala Pro Pro Pro Ala Pro Ala
65                  70                  75                  80

Gln Ser Pro Ala Pro Thr Gln Pro Pro Leu Pro Asp Ala Gly Val Gly
                85                  90                  95

Glu Leu Ala Pro Asp Leu Leu Leu Glu Gly Ile Ala Glu Asp Ser Ile
            100                 105                 110

Asp Ser Ile Ile Val Ala Ala Ser Glu Gln Asp Ser Glu Ile Met Asp
        115                 120                 125

Ala Asn Glu Gln Pro Gln Ala Lys Val Thr Arg Ser Ile Val Phe Val
130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
            180                 185                 190

Lys Ala Leu Tyr Thr Ala Lys His Ile Lys Ile Pro Cys Phe Gly Gly
        195                 200                 205

Ser His Glu Val Thr Phe Phe His Glu Tyr Arg Asp Asn Val Asp Trp
210                 215                 220

Val Phe Val Asp His Pro Ser Tyr His Arg Pro Gly Ser Leu Tyr Gly
225                 230                 235                 240

Asp Asn Phe Gly Ala Phe Gly Asp Asn Gln Phe Arg Tyr Thr Leu Leu
                245                 250                 255

Cys Tyr Ala Ala Cys Glu Ala Pro Leu Ile Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
290                 295                 300

Arg Asp Ser Arg Ser Thr Leu Val Ile His Asn Leu Ala His Gln Gly
305                 310                 315                 320

Val Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
            340                 345                 350

Leu Asp Lys Gly Glu Ala Val Asn Phe Leu Lys Gly Ala Val Val Thr
        355                 360                 365

```
Ala Asp Arg Ile Val Thr Val Ser Gln Gly Tyr Ser Trp Glu Val Thr
    370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
            405                 410                 415

Pro Thr Thr Asp Lys Cys Leu Pro His His Tyr Ser Val Asp Asp Leu
                420                 425                 430

Ser Gly Lys Ala Lys Cys Lys Ala Glu Leu Gln Lys Glu Leu Gly Leu
            435                 440                 445

Pro Val Arg Glu Asp Val Pro Leu Ile Gly Phe Ile Gly Arg Leu Asp
    450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
                485                 490                 495

Glu Gly Trp Met Arg Ser Thr Glu Ser Ser Tyr Lys Asp Lys Phe Arg
            500                 505                 510

Gly Trp Val Gly Phe Ser Val Pro Val Ser His Arg Ile Thr Ala Gly
            515                 520                 525

Cys Asp Ile Leu Leu Met Pro Ser Arg Phe Glu Pro Cys Gly Leu Asn
530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
            595                 600                 605

Pro Ser Trp Glu Gly Leu Met Lys Arg Gly Met Thr Lys Asp His Thr
    610                 615                 620

Trp Asp His Ala Pro Ser Ser Thr Ser Arg Ser Ser Gly Pro Ser
625                 630                 635                 640

Trp Thr Asn Pro Thr Ser Cys Arg Arg Gly Leu Gly Arg Ser Lys Cys
                645                 650                 655

Glu Ser Pro Ser Ala Leu Lys Thr Ser Ser Ser Phe Arg Gly Pro
            660                 665                 670

Glu Gly Tyr Pro Cys Thr Leu Arg Cys Pro Ala Thr Val Glu Ser Gln
            675                 680                 685

Cys Ala Cys Leu Leu Trp Phe Ala Gly Ser Arg Thr Tyr Asp Gly Cys
    690                 695                 700

Ala Ala Ala Ala Val Thr Ala Ser Gly Gly Arg Gln Leu Gln Phe Trp
705                 710                 715                 720

Gly Ile Arg Lys Gly Cys Ala Ala Gly Trp Leu Thr Ala Lys His His
                725                 730                 735

Ser Asp Gly Ser Leu Ser Val Arg Val Thr Ala Glu Ile Arg Asn Gln
            740                 745                 750

Leu Val Thr Leu
        755

<210> SEQ ID NO 3
<211> LENGTH: 22
<212> TYPE: DNA
```

```
<213> ORGANISM: Artificial sequence
<220> FEATURE:
<221> NAME/KEY: misc_feature
<222> LOCATION: (1)..(22)
<223> OTHER INFORMATION: primer

<400> SEQUENCE: 3
cctcccaatt caaggattag tg                                              22

<210> SEQ ID NO 4
<211> LENGTH: 20
<212> TYPE: DNA
<213> ORGANISM: Artificial Sequence, Primer
<220> FEATURE:
<221> NAME/KEY: misc_feature
<222> LOCATION: (1)..(20)
<223> OTHER INFORMATION: primer

<400> SEQUENCE: 4
cctcgcatgc agcatagcaa                                                 20

<210> SEQ ID NO 5
<211> LENGTH: 20
<212> TYPE: DNA
<213> ORGANISM: Artificial Sequence, primer
<220> FEATURE:
<221> NAME/KEY: misc_feature
<222> LOCATION: (1)..(20)
<223> OTHER INFORMATION: primer

<400> SEQUENCE: 5
tgtggctgca agtgaggagg                                                 20

<210> SEQ ID NO 6
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 6
ccagtcacaa acacgtagct acg                                             23
```